United States Patent [19]

Christensen et al.

[11] Patent Number: 4,600,713
[45] Date of Patent: * Jul. 15, 1986

[54] 1-, 6- AND 2-SUBSTITUTED-1-CARBA-2-PENEM-3-CARBOXYLIC ACIDS

[75] Inventors: Burton G. Christensen, Scotch Plains; David H. Shih, Edison, both of N.J.

[73] Assignee: Merck & Co., Inc., Rahway, N.J.

[ * ] Notice: The portion of the term of this patent subsequent to Apr. 7, 1998 has been disclaimed.

[21] Appl. No.: 557,779

[22] Filed: Dec. 5, 1983

Related U.S. Application Data

[63] Continuation of Ser. No. 363,340, Mar. 29, 1982, abandoned, which is a continuation of Ser. No. 99,451, Dec. 3, 1979, abandoned.

[51] Int. Cl.$^4$ .................. C07D 487/04; A61K 31/40
[52] U.S. Cl. ............... 514/210; 260/245.2 T; 260/239 A
[58] Field of Search ............... 260/245.2 T; 424/246; 514/210

[56] References Cited

U.S. PATENT DOCUMENTS 4,260,627 4/1981 Christensen et al. ........ 260/245.2 T
4,262,009 4/1981 Christensen et al. ........ 260/245.2 T
4,312,871 1/1982 Christensen et al. ............... 424/270

Primary Examiner—Nicholas S. Rizzo
Attorney, Agent, or Firm—Raymond M. Speer; Hesna J. Pfeiffer

[57] ABSTRACT

Disclosed are 1-, 6- and 2-substituted-1-carba-2-penem-3-carboxylic acids of the following structure:

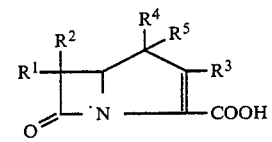

wherein $R^1$, $R^2$, $R^3$, $R^4$ and $R^5$ are, inter alia, independently selected from the group consisting of hydrogen, alkyl, cycloalkyl, cycloalkylalkyl, spirocycloalkyl, heterocyclyl, heteroaryl, aryl, and aralkyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

8 Claims, No Drawings

1-, 6- AND 2-SUBSTITUTED-1-CARBA-2-PENEM-3-CARBOXYLIC ACIDS

This is a continuation of application Ser. No. 363,340, filed Mar. 29, 1982, now abandoned, which in turn is a continuation of Ser. No. 99,451, filed Dec. 3, 1979 now abandoned.

BACKGROUND OF THE INVENTION

This invention relates to 1-, 6- and 2-substituted-1-carba-2-penem-3-carboxylic acids (I) which compounds and their pharmaceutically acceptable salts and esters are useful as antibiotics:

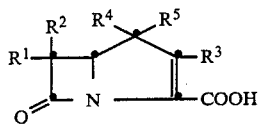

wherein $R^1$, $R^2$, $R^3$, $R^4$ and $R^5$ are independently selected from the group consisting of hydrogen, substituted and unsubstituted: alkyl, alkenyl, alkynyl, cycloalkyl, spirocycloalkyl, cycloalkylalkyl, alkylcycloalkyl, aryl, aralkyl, aralkenyl, aralkynyl, heteroaryl, heteroaralkyl, heterocyclyl and heterocyclylalkyl wherein the substituent or substituents relative to the above-named radicals are selected from the group consisting of amino, hydroxy, alkoxyl, mercapto, alkylthio, arylthio, sulfamoyl, amidino, guanidino, nitro, chloro, bromo, iodo, fluoro, cyano and carboxy; and wherein the hetero atom in the above-named heterocyclic moiety is selected from the group consisting of oxygen, nitrogen and sulphur.

The invention also relates to processes for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usuage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel class of antibiotics which are useful in animal and human therapy and in inanimate systems. These antibiotics are active against a broad range of pathogens which representatively include both gram positive bacteria such as *S. aureus*, Strep. pyogenes, and *B. subtilis*, and gram negative bacteria such as *E. coli*, Pseudomonas, *Proteus morganii*, Serratia and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

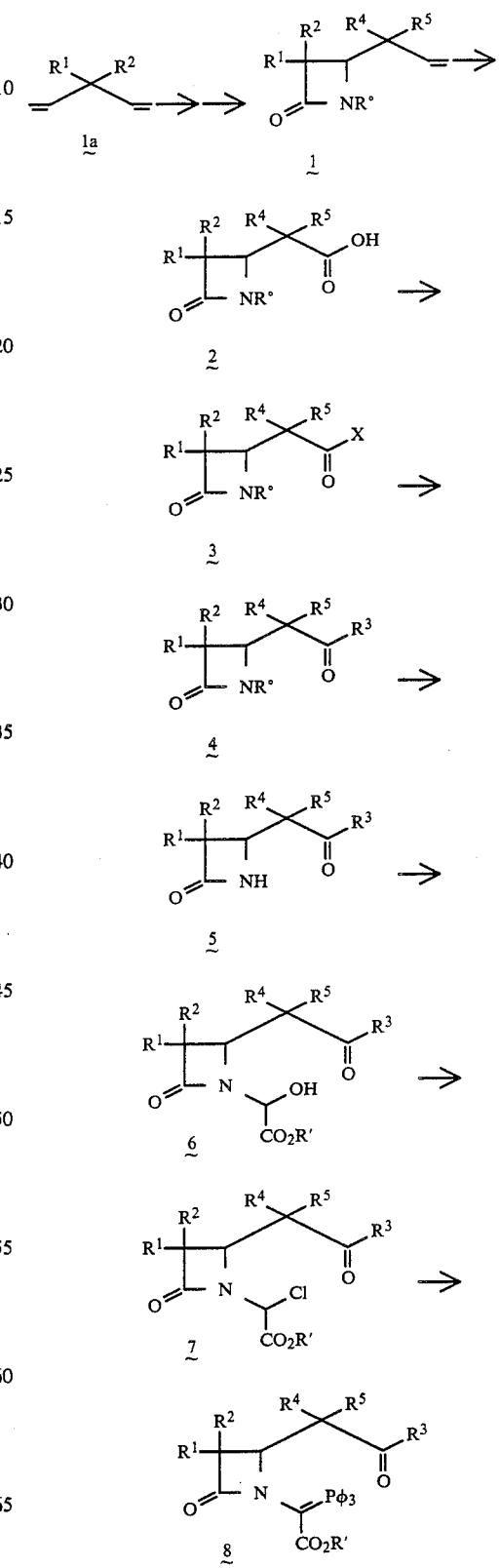

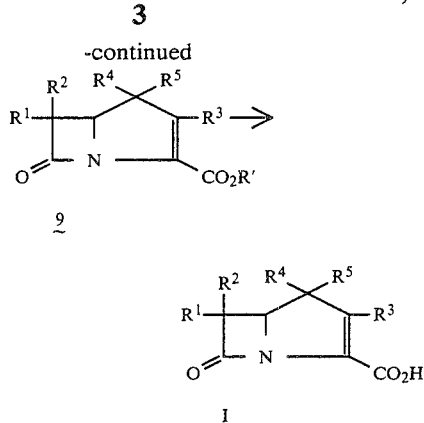

9

<br/>

I

In words relative to the above reaction diagram, a suitably substituted azetidinone 1 is oxidized by treating 1 in a solvent such as methylenechloride, methanol, chloroform, or the like, with an oxidizing agent such as ozone, or the like, at a temperature of from $-100°$ to $0°$ C. for from 0.1 to 4 hours, followed by treating the crude product with an oxidizing agent such as m-chloroperchenzoic acid, hydrogen peroxide, peracetic acid, or the like, at a temperature of from $0°$ C. to $100°$ C. for from 1 to 100 hours.

The sequence 2→3→4 may be achieved by well-known methods for converting a carboxylic acid to a ketone such as by activating a carboxylic function with dicyclohexylcarbodiimide, ethylchloroformate, 2-fluoropyridine, 1-fluoro-2,4-dinitrobenzene, thionyl chloride, oxalyl chloride, or the like followed by the neucleophilic displacement of the leaving group with a carbon neucleophile such as $R^3{}_2CuMgX°$, $R^3MgX°$, $LiCuR^3{}_2$, $R_2{}^3Cd$ or the like to give the desired ketone 4, ($X°$ is bromo or chloro). Or preferably by displacement of the chloride with a thiophenol or 2-mercaptopyridine to give a stable thioester 3 wherein X is phenylthio or pyridylthio which may subsequently be reacted with a Grignard reagent to yield the ketone 4.

Removal of protecting group $R°$ (4→5) is accomplished by acidic aqueous hydrolysis of 4 in a solvent such as methanol, ethanol, tetrahydrofuran, dioxane, or the like, in the presence of an acid such as hydrochloric, sulfuric, acetic or the like at a temperature of from $0°$ to $100°$ C. for from 2 to 18 hours.

The azetidinone 5 is then reacted with a glyoxyalate ester such as benzyl glyoxalate to give 6. In addition to benzyl, R' may be any readily removable protecting group or it may be a pharmaceutically acceptable ester moiety. The reaction 5→6 is conveniently carried out in a solvent such as benzene, toluene, xylene and the like at a temperature of from about $25°$ C. to reflux for from 2 to 10 hours. There is no criticality as to the precise identity of the solvent, provided only that it adequately solubilizes the reactants and be inert or substantially inert to the desired course of reaction. The halogenation reaction 6→7 may be conducted by any of any of a variety of well-known halogenation means. Suitable reagents include: $SOCl_2$, $POCl_3$, oxalyl chloride and the like. A preferred means of chlorination involves treating 6 in a solvent such as tetrahydrofuran (THF), ether, $CH_2Cl_2$ and the like with thionylchloride in the presence of 1 to 2 equivalents (relative to the thionylchloride) of a base such as pyridine, triethylamine, quinoline and the like. Typically, the reaction is conducted at a temperature of from $-30°$ to $25°$ C. for from 0.5 to 1 hour. The resulting 7 is isolated, if desired, by conventional procedures for later reaction, 7→8. The intermediate 8 is prepared by treating 7 in a solvent such as dimethylformamide (DMF), dimethylsulfoxide (DMSO), THF, dimethoxyethane (DME) and the like with 1 to 1.5 equivalents of a phosphine such as triphenylphosphine, tributylphosphine, triethylphosphine, tris-(2-cyanoethyl) phosphine or the like. Typically the reaction is conducted under a nitrogen atmosphere at a temperature of from $-20°$ to $25°$ C., for from 0.5 to 2 hours.

Typically, the closure step 8→9 is conducted by heating 8 from $100°$–$160°$ C. in a solvent such as benzene, toluene, dioxane, xylene, or DMF. The carboxyl deblocking step 9→(I) may be achieved by a number of well-known procedures such as hydrolysis, hydrogenation, or photolysis of a suitable R' group. Suitable hydrogenation catalysts for deblocking include the platinum metals and their oxides such as palladium on carbon and the like; suitable solvents for the hydrogenation include methanol, dioxane/$H_2O$, ethanol/$H_2O$, and the like in the presence of hydrogen at a pressure of from 1 to 50 atmospheres; the hydrogenation is typically conducted for from 5 min. to 4 hours at a temperature of about $25°$ C. in the optional presence of a mild base such a sodium bicarbonate or the like.

The above-mentioned glyoxalate esters used to react with 5 can be prepared by oxidation of the corresponding tartaric acid diesters with oxidants such as periodic acid or lead tetracetate in a solvent such as THF, benzene, methylene chloride at $-20°$ to $25°$ for ½ to 4 hours. The tartarate esters are prepared from dilithio tartarate or disodio tartarate by reaction with R'X wherein X is chloro, bromo or iodo and R' is as defined above in a solvent such as DMF or DMSO at $25°$ to $70°$ C. for from 4 to 48 hours. As noted above, R' may be a pharmaceutically acceptable ester moiety which is not subjected to the removal step 9→I.

Especially preferred pharmaceutically acceptable salts and esters involving the carboxyl group of compounds of the present invention (I) are disclosed and claimed in U.S. patent application Ser. No. 861,314 (filed 12-16-77), which application is directed, inter alia, to pharmaceutically acceptable salts and esters of the carboxyl group of thienamycin. It is precisely these salts and esters which are preferred in the present invention and they are prepared in a manner analogous to that disclosed in U.S. patent application Ser. No. 861,314, which is incorporated herein by reference. Thus, especially preferred salts include sodium, potassium, ammonium, and the like; and especially preferred esters include pivaloxymethyl p-t-butylbenzyl, 5-indanyl, 3-phthalidyl, 3-methyl-2-butenyl, and the like.

PREPARATION OF STARTING MATERIAL 1 AND 1a

With respect to starting reagent 1a, its preparation is generally described in *J. Amer. Chem. Soc.*, 74, 661 (1952) by E. B. Reid and T. E. Gompf, *J. Org. Chem.*, 23,1,063 (1958) by R. Ciola and K. L. Burwell, Jr., and Belgium Pat. No. 632,193 (1963) by R. Polster and E. Scharf. The following scheme summarizes the preparation of 1.

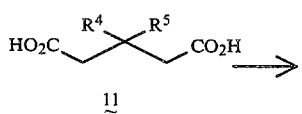

11

-continued

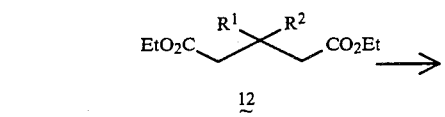

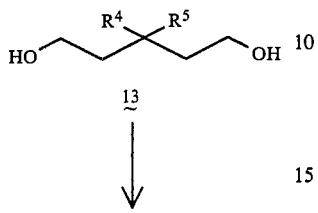

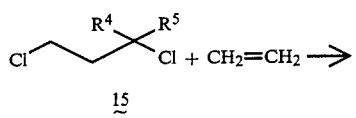

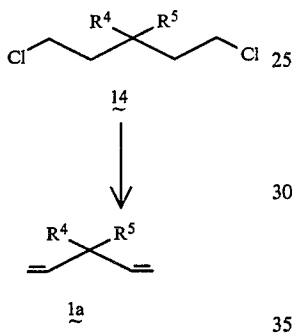

In words relative to the above scheme, the diester 12 is prepared by treating the diacid 11 with thionyl chloride at reflux for two hours followed by reacting with ethanol at 80° C. for 4 hours. Reduction of the diester 12 with lithium alumium hydride in ether at reflux for 4 hours followed by hydrolysis with 10% NaOH gives diol 13 which on further reaction with thionyl chloride to give dichloride 14. The dichloride 14 can be alternatively prepared by treating 15 with ethylene in the presence of alumium chloride. Treatment of the dichloride 14 with base such as 2-methylquinoline, DBU or sodium hydroxide in polyethylene glycol gives the expected 3-substituted 1,4-pentadiene 1a.

Preparation of 1 is summarized in the following scheme:

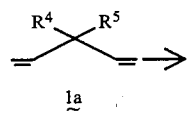

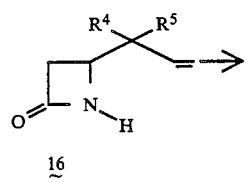

-continued

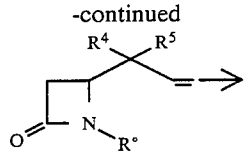

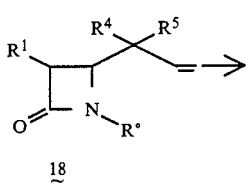

In words relative to above scheme, the substituted azetidinone 16 is prepared by reacting a 3-substituted 1,4-pentadiene 1a with chlorosulfonylisocyanate at 25° C. to 60° C. in a pressure bottle for 3–12 days, then the resulting mixture is hydrolyzed with aqueous sodium sulfite solution between pH 6.5–7.5 at 0° C. to 25° C. for from 5 min. to 60 min.

Azetidinone 16 is transformed (16→17) to establish the protecting group R° which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically R° is established by treating 16 in a solvent such as dimethylformamide, acetonitrile, hexamethylphosphoramide, tetrahydrofuran and the like with a silylating agent such as t-butyldimethylchlorosilane, t-butyldiphenylchlorosilane, triphenylchlorosilane, and the like at a temperature of from −20° C. to 25° C. for from 0.5 to 24 hours in the presence of a base such as triethylamine, diisopropylethylamine, or imidazole.

Alkylation of 17 provides 18. Typically, 17 is treated with a strong base such as lithium diisopropylamide, sodium hydride, phenyl lithium butyl lithium or the like in a solvent such as tetrahydrofuran (THF), ether, dimethoxyethane and the like at a temperature of from −80° C. to 0° C., whereupon the alkylating agent of choice, $R^1X$ is added ($R^1$ is as described above and X is chloro or bromo; alternatively the alkylating agent may be $R^1$-tosylate, $R^1$-mesylate or an aldehyde or ketone such as acetaldehyde and the like) to provide monoalkylated species 18. When desired dialkylated species 1 may be obtained from 18 by repeating the alkylating procedure, 17→18.

In the generic description of the present invention (I, above), the substituents $R^1$, $R^2$, $R^3$, $R^4$, and $R^5$ are preferably selected from the group consisting of hydrogen; substituted and unsubstituted: straight and branched loweralkyl having from 1 to 10 carbon atoms; spirocycloalkyl and cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl such as phenyl and naphthyl; aralkyl such as benzyl, phenethyl and the like; heterocyclyl (saturated and unsaturated) comprising mono- and bicyclic structures having from 5 to 10 ring atoms wherein one or more of the hetero atoms is selected from oxygen, nitrogen or sulphur, such as thiophene, imidazolyl, tetrazolyl, furyl and the like; heterocyclylalkyl which comprises the immediately preceding heterocyclyl moieties and the alkyl moiety comprises from 1 to 10 carbon atoms; the substituent (or substituents) relative to the above-named radicals is selcted from the group consisting of amino, hydroxyl, cyano, carboxyl, nitro, chloro, bromo, fluoro, lower alkoxy having from 1 to 6 carbon atoms, mercapto, perhaloloweralkyl such as trifluoromethyl, loweralkylthio, guanidino, amidino, sulfamoyl, and N-substituted: sulfamoyl, amidino and guanidino wherein the N-substituent is loweralkyl having from 1 to 6 carbon atoms or aryl having 6–10 carbon atoms.

The preferred esters used as protecting groups are those where R' is benzyl, p-nitrobenzyl, o-nitrobenzyl, t-butyl, bromo-t-butyl, t-butyl-dimethylsilyl, trimethylsilyl, trichloroethyl; or R' represents pharmaceutically acceptable ester moieties such as pivaloyloxymethyl, allyl, methallyl, (2-methylthio)-ethyl, 3-methyl-2-butenyl, p-t-butylbenzyl, 5-indanyl, 3-phthalidyl.

Especially preferred embodiments of the present invention are those, as defined above, except that any unsubstituted amino group borne on radical $R^3$ of Structure I is derivatized according to the teachings of Belgium Pat. No. 848,545 (issued 5-20-77); the resulting amino group being represented thusly (partial structure):

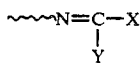

wherein X and Y are defined by the publication; species wherein X is H or lower alkyl and Y is $NH_2$ are especially preferred.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, loweralkanolamines, di-loweralkanolamines, lower alkylenediamines, N,N-diaralkyl lower alkylenediamines, aralkylamines, amino substituted lower alkanols, N,N-di-loweralkylamino substituted lower alkanols, amino-, polyamino and guanidino-substituted lower alkanoic acids and nitrogen containing herocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

Salts of the amino group carried in certain species of I on side chains $R^1$, $R^2$, $R^3$, $R^4$ and $R^5$ are also contemplated. Such pharmaceutically acceptable acid addition salts are derived from organic and inorganic acids such as HCl, HBr, citric, tartaric and the like.

The salts can be mono-salts such as the mono-sodium salt obtained by treating one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit dosage pharmaceutical forms. Also, they may be combined with other drugs to provide compositions having a broad spectrum of activity.

The novel 1-,6- and 2-substituted-1-carba-2-penem-3-carboxylic acids of the present invention are valuable antimicrobial substances which are active against various gram-positive and gram-negative pathogens. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules, suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella penumoniae, Bacillus subtilis, Salmonella typhosa,* Pseudomonas and *Bacterium proteus*. The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medica and dental equipment and as bactericides in industrial applications, for example in waterbased pains and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspension or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gleatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semisolid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg of active ingredient per kg. of body weight.

The instant compositions may be administered in several unit dosage forms as, for example, in solid or liquid orally ingestible dosage form. The compositions per unit dosage, whether liquid or solid may contain from 0.5% to 99% of active material, the preferred range being from about 10–60%. The composition will generally contain from 15 mg. to about 1500 mg. of the active ingredient; however, in general, it is preferably to employ a dosage amount in the range of from about 100 mg. to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention. All reaction temperatures are in °C.

EXAMPLE 1

Preparation of 3,3-Dimethyl-1,4-pentadiene

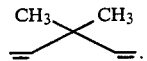

PROCEDURE A $\beta,\beta$-Dimethylglutaric acid (obtained from Aldrich Chemical Company) (one mole), is refluxed for 2 hours with thionyl chloride (68% excess). After removal of excess thionyl chloride, absolute ethanol (109% excess) is added slowly. The mixture is refluxed for 3 hours then distilled to collect the product, diethyl $\beta,\beta$-dimethylglutarate (98% yield).

To a suspension of lithium aluminum hydride (24 g) in ether (860 ml) is added dropwise with rapid stirring a solution of diethyl $\beta,\beta$-dimethylglutarate (124 g in 250 ml ether). The mixture is refluxed for 6 hours, then cooled to room temperature. Water (25 ml) is added slowly. The mixture is then titrated with 10% NaOH until a clear organic layer is obtained. The organic layer is separated, dried over anhydrous sodium sulfate then evaporated in vacuo to give the resulting diol as an oil (90% yield), b.p.95° at 1.0 mm. The 3,3-dimethyl-1.5-pentanediol (0.5 mole) is treated with thionyl chloride (1.05 mole) at reflux for 3 hours. After removal of excess thionyl chloride in vacuo, the 3,3-dimethyl-1,5-dichloropentane is obtained (90% yield).

3,3-Dimethyl-1,5-dichloropentane (41 g) is added dropwise at 170° C. to a mixture of 48 g of sodium hydroxide and 40 g of polyethylene glycol tetramer and the mixture is distilled to give 3,3-dimethyl-1,4-pentadiene (66%).

PROCEDURE B

At $-40°$ C., 1,3-dichloro-3-methylbutane (50 g) is mixed with aluminum chloride (5 g). The ethylene is bubbled through the mixture for 4 hours. The mixture is allowed to warm to room temperature and hydrolyzed with water. The mixture is extracted with ethyl acetate to give 3,3-dimethyl-1,5-dichloropentane.

A mixture of 0.5 mole of 3,3-dimethyl-1,5-dichloropentane, 2-methylquinoline (2 moles), and sodium iodide (0.1 mole) is refluxed in a flask equipped with a Vigreaux column at the top of which is a condenser and take-off. The diolefin 1 is collected during 8 hrs reaction. The product is dried over anhydrous sodium sulfate.

EXAMPLE 2

Preparation of 3-methyl-1,4-pentadiene

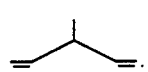

Following the procedure of Example 1(a), but replacing $\beta,\beta$-dimethylglutaric acid with an equivalent amount of β-methylglutaric acid, 3-methyl-1,4-pentadiene is obtained.

EXAMPLE 3

Preparation of 4-(1,1-dimethyl-pro-2-enyl)azetidin-2-one

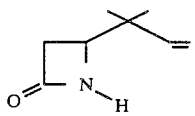

In a sealed tube, 3,3-dimethyl-1,4-pentadiene (9.6 g) and chlorosulfonyl isocyanate (14.2 g) are allowed to stand at room temperature for 10 days. The resulting mixture is diluted with methylene chloride and added slowly to a stirred aqueous solution which contains 20 g of Na₂SO₃ and 50 g of K₂HPO₄ at 0°-5° C. for 30 min. The organic layer is separated and dried over MgSO₄. After evaporation, the crude product is chromatographed on silica gel GF eluting with EtOAc to give 3.

EXAMPLE 4

Preparation of 4-(1-methyl-pro-2-enyl)azetidin-2-one

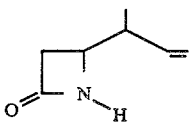

Following the procedure of Example 3, but replacing 3,3-dimethyl-1,4-pentadiene with 3-methyl-1,4-pentadiene, the title compound 4 is obtained.

EXAMPLE 5

Preparation of 5

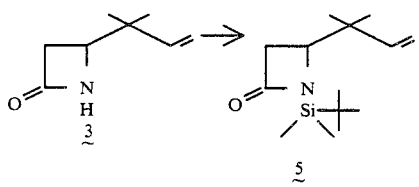

t-Butyldimethylchlorosilane (7.51 g) is added in one portion to an ice-cold, stirred solution of 4-(1,1-dimethyl-prop-2-enyl)azetidin-2-one (6.54 g) and triethylamine (5.04 g) in anhydrous dimethylformamide (100 ml). The reaction mixture is stirred at 0°-5° C. for 1 hour and then allowed to warm to room temperature. Most of the solvent is removed under vacuum to give a residue which is partitioned between diethyl ether (250 ml) and water. The ethereal phase is washed with 2.5N hydrochloric acid (50 ml), water (3×50 ml), and brine, dried with magnesium sulfate, filtered and evaporated under vacuum to provide an oil which is purified by chromatography on silica gel (20% ether in petroleum ether) to yield 5.

EXAMPLE 6

Preparation of 6

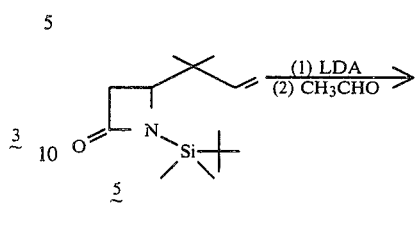

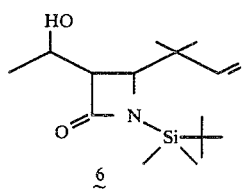

n-Butyllithium in hexane (26.25 mmol) is added slowly by syringe to a solution of diisopropylamine (26.25 mmol) in anhydrous tetrahydrofuran (100 ml) at −78° C. The resulting solution is stirred for 15 min. prior to the addition of a solution of 5 (25.0 mmol) in anhydrous tetrahydrofuran (25 ml). After stirring for 15 min. at −78° C., acetaldehyde (75 mmol) is added by syringe and the resulting solution is stirred at −78° C. for 5 min. Saturated aqueous ammonium chloride solution (15 ml) is added by syringe and the reaction mixture is allowed to warm to room temperature, then diluted with ether (250 ml) and washed with 2.5N hydrochloric acid solution (2×50 ml), water (100 ml) and brine and dried over magnesium sulfate. Solvents are removed in vacuo and the residue is chromatographed on silica gel (1:1, ether:-petroleum ether) to give the expected product 6.

EXAMPLE 7

Preparation of 7

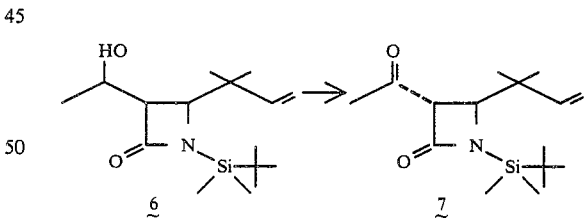

A. Trifluoroacetic anhydride (7.5 mmol) is added dropwise by syringe to a solution of dimethylsulfoxide (10 mmol) in anhydrous methylene chloride (15 ml) at −78° C. The resulting mixture is stirred at −78° C. for 20 min. A solution of 6 (5.0 mmol) in methylene chloride (15 ml) is added by syringe and the cooling bath is removed. After an additional 1 hr., the reaction mixture is diluted with methylene chloride (100 ml), washed with water (50 ml) and brine and dried over magnesium sulfate. Removal of solvents in vacuo yields crude product which is chromatographed on silica gel (2:1, petroleum ether:ether) to yield 7.

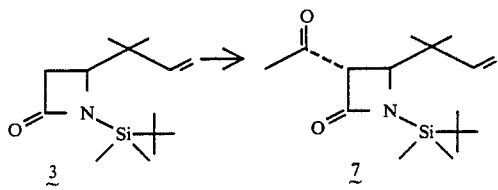

B. n-Butyllithium in hexane (4.10 mmol) is added by syringe to a solution of diisopropylamine (4.10 mmol) in anhydrous tetrahydrofuran (16 ml) at −78° C. The resulting solution is stirred at −78° C. for 15 min. prior to the addition of a solution of 1-(t-butyldimethylsilyl)-4-(1,1-dimethyl-prop-2-ene)-azetidin-2-one 3 (2.0 mmol) in anhydrous tetrahydrofuran (2 ml). After an additional 15 min. at −78° C., the reaction mixture is added via a Teflon tube to a mixture of N-acetylimidazole (4.1 mmol) in anhydrous tetrahydrofuran (16 ml) at −78° C. The resulting yellow reaction mixture is stirred at −78° C. for 15 min., then quenched by addition of saturated aqueous ammonium chloride solution (10 ml). The reaction mixture is diluted with ether (100 ml) and washed with 2.5N hydrochloric acid solution (25 ml) water (25 ml) and brine. The organic phase is dried over magnesium sulfate and concentrated in vacuo to yield an oil. This material is chromatographed on silica gel (2:1 petroleum ether:ether) to yield 7.

EXAMPLE 8

Preparation of 6

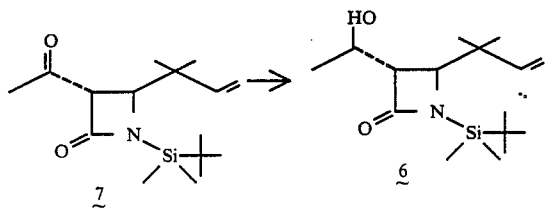

K-Selectride (potassium tri-(sec)-butylborohydride) in tetrahydrofuran (4.8 mmol) is added by syringe to a mixture of potassium iodide (2.0 mmol) and 7 (2.0 mmol) in anhydrous ether (20 ml) at room temperature. The resulting mixture is stirred at room temperature for 2.5 hours, then quenched by addition of glacial acetic acid (9.6 mmol). The resulting mixture is diluted with ethylacetate (100 ml) and filtered through celite. Removal of solvents in vacuo gives an oil which is chromatographed on silica gel (1:1 ether:petroleum ether) to yield 1.90 g (95%) of 6.

EXAMPLE 9

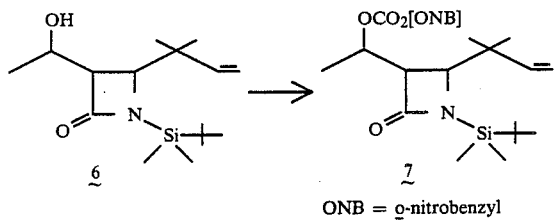

ONB = o-nitrobenzyl

Under anhydrous conditions at 0° C. a solution of 6 (3.50 g) in 60 ml methylene chloride is treated with 4-dimethylaminopyridine (3.32 g) and o-nitrobenzylchloroformate (5.88 g). The mixture is allowed to warm to room temperature and stirred for 1 hr. The resulting mixture is washed with 0.1N HCl, water, brine and water. The organic layer is separated, dried over Na$_2$SO$_4$ and allowed to evaporate in vacuo to give crude products. The crude products dissolved in 20 ml ether and chilled at −5° C. give the o-nitrobenzyl alcohol (0.5 g) which is separated by filtration. The purification by HPLC (silica gel) eluting with 40% ethylacetate/cyclohexane to give 7.

EXAMPLE 10

Preparation of 8

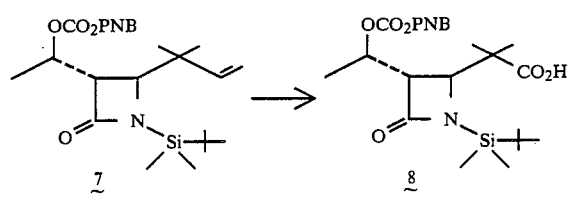

A solution of 7 (3.0 mmol) in dry methylene chloride (30 ml) is cooled to −78° C. (dry ice-acetone) and a stream of ozone is bubbled through until the reaction mixture becomes blue. The ozone flow is then stopped and the reaction is purged by bubbling through nitrogen until the blue color disappears. Solid m-chloroperbenzoic acid (3.0 mmol) is added and the cold bath is removed. When the reaction mixture reaches room temperature, the flask is fitted with a reflux condenser and the mixture is heated at reflux for three days. Removal of solvents in vacuo gives crude product which is chromatographed on silica gel (2% glacial acetic acid in methylene chloride) to 8.

EXAMPLE 11

Preparation of 11

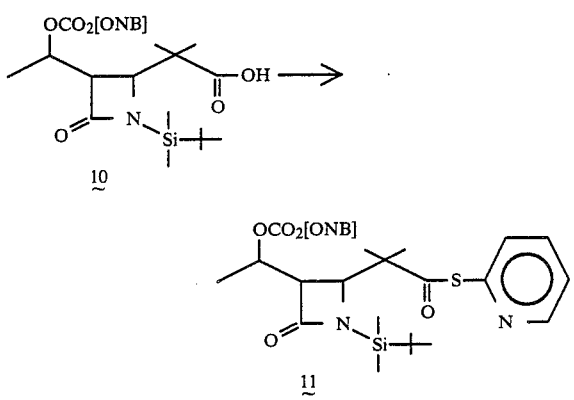

The azetidinone 10 (0.851 g) is dissolved in 20 ml CH$_2$Cl$_2$ and cooled to 0° C. under N$_2$. Oxalyl chloride (0.8 ml) is added dropwise over 5 min. followed by 1 drop of DMF. The mixture is stirred at 0° for 5 min. and then at 25° C. for 15 min. The solvent and excess oxalyl chloride are evaporated under reduced pressure. The residue is the desired acid chloride. The acid chloride is dissolved in 20 ml CH$_2$Cl$_2$ and cooled to 0°, under N$_2$. Mercapatopyridine (0.4 g) and pyridine (0.8 ml) are added. The reaction mixture is stirred at 0° C. for 5 min., then allowed to warm to room temperature. The mixture is diluted with CH$_2$Cl$_2$ and washed with water, dried over $Na_2SO_4$ and evaporated in vacuo. The residue is chromatographed on silica gel using 50% $EtOAc/C_6H_5$ as eluant, to givee the thio ester 11.

EXAMPLE 12

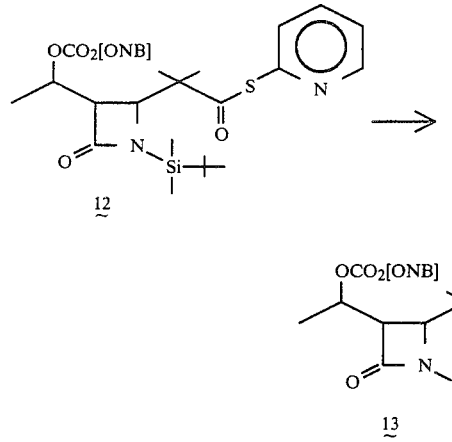

The thio ester 12 (64 mg) in 2 ml THF is treated with a solution of cyclopropyl magnesium bromide (0.25M in $Et_2O$, 2.6 ml). The mixture is allowed to stir at 0° for 1 hour. A saturated $NH_4Cl$ aqueous solution is added and the mixture is allowed to stir for 10 minutes. The organic phase is separated. The aqueous phase is extracted twice with $CH_2Cl_2$. The combined organic extracts are dried and evaporated. Preparative t.l.c. of the residue using silica gel and 50% EtOAc/benzene gives the desired product 13.

EXAMPLE 13

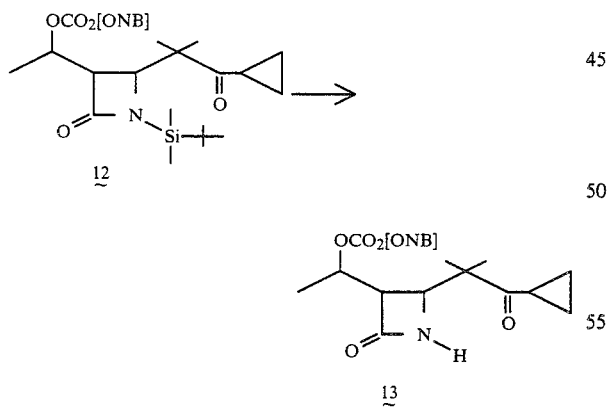

A solution of 12 (1.0 mmol) in 20 ml of MeOH is cooled to 0° C. Hydrochloric acid (2.5N, 1 eq) is added and the resulting solution is stirred at 0° C. for 1 hr., then allowed to warm to room temperature. The mixture is diluted with ethyl acetate (25 ml), washed with water (10 ml) and brine, dried over magnesium sulfate and concentrated in vacuo to give 13.

EXAMPLE 14

Preparation of 14

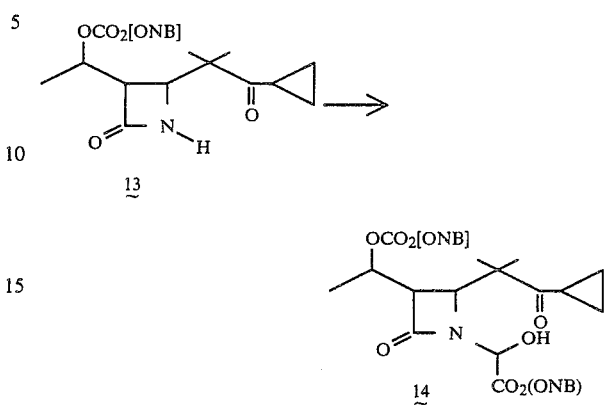

The azetidinone 13 (0.8 g) and p-nitrobenzyl glyoxylate hydrate (1.5 g) are refluxed in benzene (100 ml) for 6 hrs. The reaction apparatus is equipped with a Dean-Stark trap of removal of water azeotropically. The solution is cooled, evaporated, and chromatographed on silica gel eluting with 50% EtOAc/cyclohexane to give product 14.

EXAMPLE 15

Preparation of 16

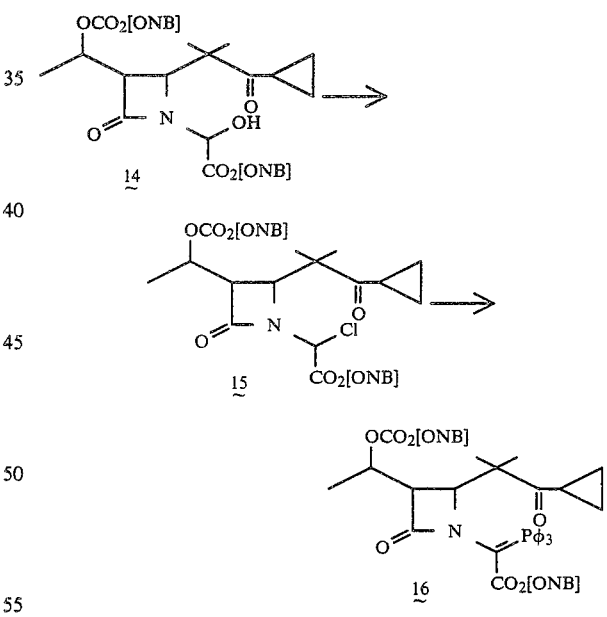

Under $N_2$, at $-20°$ C., the carbinal 14 (0.8 g) in 5 ml THF is treated with thionyl chloride (204 mg) and pyridine (136 mg) for 10 min., then the mixture is allowed to warm to room temperature. The mixture is diluted with 10 ml benzene and filtered from solids. Evaporated of filtrate in vacuo gives the expected chloride which is then treated with triphenylphosphine (468 mg) in 5 ml DMF and stirred at room temperature for 1 hr. After evaporation of solvent in vacuo, the residue is dissolved in 70 ml $CH_2Cl_2$ and washed with 0.5M sodium phosphate buffer (pH 6.9). The organic layer is separated, dried over $MgSO_4$ and chromatographed on silica gel eluting with 30% ethyl acetate/CH₂Cl₂ to give 16.

EXAMPLE 16

Preparation of 17

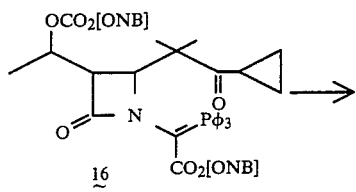

16

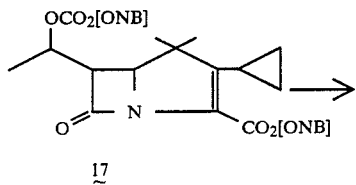

17

The ylide 16 (61 mg) is dissolved in 3 ml xylene and heated at 140° under N₂ for 1.5 hr. The mixture is cooled to 25° C. Xylene is removed under reduced pressure. The residue chromatographed on silica gel plates gives the desired product 17.

EXAMPLE 17

Preparation of 18

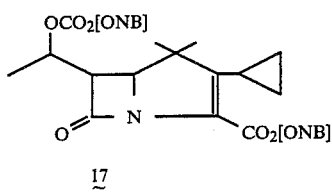

17

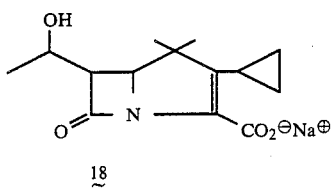

18

The carbapenem ester 17 (10 mg) is dissolved in 1 ml dioxane. To the solution is added 1 ml water, 0.2 ml ethanol, 10 mg NaHCO₃, and 5 mg 10% Pd/C. The mixture is hydrogenated for 20 min. at 40 psi.

The mixture is filtered from catalyst, and the filtrate is extracted with 3×5 ml ether. The aqueous layer is separated and chromatographed on an XAD-2 column eluted with water then 10% THF/water to give the title compound 18.

EXAMPLE 18

Preparation of 19

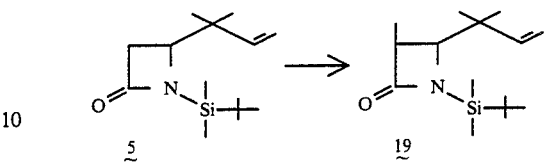

THF, 20 ml, is placed under N₂, treated with 1.54 ml diisopropylamine and cooled to −78° C. A solution of n-butyl lithium 1.97M in hexane (5.6 ml) is added dropwise over 5 min. The reaction mixture is stirred at −78° C. for 10 min. and then treated with 5 (2.14 g) in 15 ml THF which is added dropwise over 5 min. After another 10 min. hexamethylphosphoramide (1.97 ml) is added. The mixture is stirred another 10 min., then treated with 2 ml of methyl iodide. The reaction mixture is stirred at −78° C. for 15 min. and allowed to warm to 25° C. and stirred for 15 min. The reaction mixture is diluted with EtOAc, washed once with pH7 phosphate buffer then dried and evaporated. The residue is chromatographed on silica gel using 25% EtOAc/C₆H₆ as eluant to give 19.

EXAMPLE 19

Preparation of 20

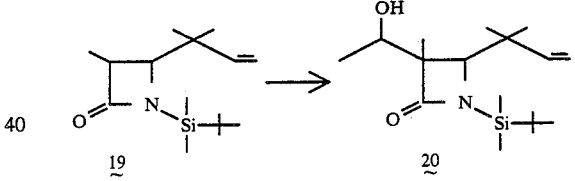

To a solution of 1.1 equivalents of freshly prepared lithium diisopropylamide in anhydrous tetrahydrofuran under a nitrogen atmosphere at −78° C. is added a solution of 19 in anhydrous tetrahydrofuran which has been cooled to −78° C. After two minutes, the resulting lithium enolate is treated with excess acetaldehyde introduced as a gas just above the surface of the stirred solution. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethyl acetate/benzene gives 20.

EXAMPLE 19a

Following the procedure of the foregoing Examples, the following substituted azetidinones useful in the preparation of the compound of the present invention are obtained when the suggested substitution of reagents is made.

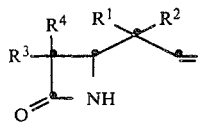
| Compound | R¹ | R² | R³ | R⁴ |
|---|---|---|---|---|
| (1.) | $CH_3$ | $CH_3$ | H | 2-$NO_2$-$C_6H_4$-$CH_2$-O-C(O)-O-$CH_2$- |
| (2.) | $CH_3$ | Et | H | $CH_3$ |
| (3.) | $CH_3$ | cyclopropyl | H | $C_6H_5$C(O)- |
| (4.) | $CH_3$ | $C_6H_5CH_2$ | H | $CH_3$C(O)- |
| (5.) | $CH_3$ | $CH(CH_3)_2$ | H | $CH(CH_3)_2$ |
| (6.) | $CH_3$ | Ph | H | $CH(CH_3)N_3$ |
| (7.) | $CH_3$ | $CH_3CH_2CH_2$ | $CH_3$ | $CH_3CH(OCO_2CH_2$-2-$NO_2$-$C_6H_4)$ |
| (8.) | Et | Et | $CH_3CH_2$ | $CH_3CH_2(OCO_2CH_2$-3-$NO_2$-$C_6H_4)$ |
| (9.) | $CH_3$ | H | $CH_3$ | $CH_3$C(O)- |
| (10.) | Et | $CH_3$ | H | $CH_3CH(OCO_2CH_2$-2-$NO_2$-$C_6H_4)$ |
| (11.) | Et | Et | $CH_3$ | $CH_3CH(OCO_2CH_2$-2-$NO_2$-$C_6H_4)$ |
| (12.) | cyclopropyl | $CH_3$ | $CH_3$ | $CH_3CH_2(OCO_2CH_2$-2-$NO_2$-$C_6H_4)$ |

-continued

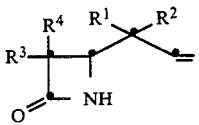

| Compound | R¹ | R² | R³ | R⁴ |
|---|---|---|---|---|
| (13.) | CH₃ | CH₃ | H | CH₂(CH₂—)CH—OCO₂CH₂—(2-NO₂-C₆H₄) |
| (14.) | CH₃ | Et | H | (CH₃)₂CH—OCH₂SCH₃ (iPr with OCH₂SCH₃) |
| (15.) | H | cyclopropyl | H | PhCH(—)OCO₂CO₂CH₂—(2-NO₂-C₆H₄) |
| (16.) | (CH₃)₂CH(CH₃)— | CH₃ | H | Ph— |
| (17.) | CH₃ | CH₃ | H | 4-pyridyl |
| (18.) | CH₃ | H | H | 4-pyridyl |
| (19.) | CH₃ | Et | H | CH₃CH(—)SCO₂CH₂—(2-NO₂-C₆H₄) |
| (20.) | R¹ + R² = SPIROCYCLOPROPYL | | H | (CH₃)₂CH—OCO₂PNB [PNB = p-nitrobenzyl] |
| (21.) | CH₂CH₂Br | CH₃ | H | (CH₃)₂CH—OCO₂PNB |

EXAMPLE 20

Following the standard procedure developed by the foregoing Examples 1–16, the following 1,2,6-substituted-1-carbadethiapen-2-em-3-carboxylic acid (I) are obtained by strict analogy when the suggested substitution of reagents is made.

TABLE V $$\text{Structure I: } R^1R^2\text{-substituted azetidinone with } R^4, R^5, R^3\text{-COOR side chain}$$

| Compound | R¹ | R² | R³ | R⁴ | R⁵ | R |
|---|---|---|---|---|---|---|
| 1. | CH₃-CH(OH)- | H | -C₆H₄-CH₂NHC(=NH)CH₃ (para) | CH₃ | CH₃ | H |
| 2. | CH₃-CH(OH)- | H | -C₆H₅ | CH₂CH₂NH₂ | CH₃ | H |
| 3. | CH₃-CH(OH)- | H | -C₆H₄-NH₂ (para) | CH₃ | C₂H₅ | H |
| 4. | CH₃-CH(OH)- | H | -C₆H₄-CH₂NH₂ (meta) | CH₃ | cyclopropyl | -CH₂OC(=O)CMe₃ |
| 5. | CH₃-CH(OH)- | H | -C₆H₄-CH₂NHC(=NH)NH₂ (para) | CH₃ | CH₃ | H |
| 6. | CH₃-CH(OH)- | H | -CH₂CH₂NHC(=NH)-CH₃ | CH₃ | CH₃ | H |
| 7. | CH₃-CH(OH)- | H | -CH(CH₃)CH₂CH₂NH₂ | CH₃ | CH₃ | H |
| 8. | CH₃-CH(OH)- | H | -CH₂CH₂CH₂NHC(=NH)H | CH₃ | CH₃ | H |
| 9. | CH₃-CH(OH)- | H | cyclopropyl-NH₂ | CH₃ | CH₃ | H |
| 10. | CH₃-CH(OH)- | CH₃ | cyclopropyl-NHCH(=NH) | CH₃ | CH₃ | H |
| 11. | CH₃-CH(OH)- | CH₃ | -CH=CH-CH₂NHC(=NH)-CH₃ | C₂H₅ | CH₃ | H |
| 12. | CH₃-CH(OH)- | H | -CH=CH-CH₂NHC(=NH)-CH₃ | C₂H₅ | CH₃ | H |
| 13. | CH₃-CH(OH)- | H | -CH₂-(2-pyridyl) | CH₃ | CH₃ | H |
| 14. | CH₃-CH(OH)- | H | -CH₂-(4-pyridyl) | CH₃ | CH₃ | H |

TABLE V-continued $$\text{structure with } R^1, R^2, R^4, R^5, R^3, \text{COOR substituents on } \beta\text{-lactam fused ring}$$

I

| Compound | R¹ | R² | R³ | R⁴ | R⁵ | R |
|---|---|---|---|---|---|---|
| 15. | CH₃-CH(OH)- (H) | H | -CH₂-C(=CH-N=)(S)-CH₃ (thiazole) | CH₃ | CH₃ | Na |
| 16. | -CH₂OH | H | -CH₂-(N-methylpyrrolidin-2-yl) | CH₃ | CH₃ | H |
| 17. | -CH₂OH | CH₃ | -C₆H₄-CH₂NH₂ | CH₃ | Et | H |
| 18. | -CH₂OH | CH₃ | -CH₂CH₂NHCH=NH | CH₃ | CH₃ | H |
| 19. | CH₃-CH(NH₂)- (H) | H | CH₃ | CH₃ | CH₃ | H |
| 20. | CH₃-CH(NH₂)- (H) | H | -C₆H₅ | CH₃ | CH₃ | H |
| 21. | CH₃-CH(NH₂)- (H) | H | -cyclopropyl | C₂H₅ | CH₃ | H |
| 22. | -CH₂NH₂ | CH₃ | -CH(CH₃)₂ | CH₃ | CH₃ | H |
| 23. | C₂H₅-CH(NH₂)- (H) | H | -C₆H₄-OMe | CH₃ | CH₂CH₂CH₃ | H |
| 24. | C₂H₅-CH(OH)- (H) | H | -CH₂CH(CH₃)-NH₂ | CH₃ | -cyclopropyl | H |
| 25. | (CH₃)₂CH-CH(OH)- (H) | H | -cyclopropyl-CH₂NH₂ | CH₃ | CH₃ | H |
| 26. | (CH₃)₂CH-OH (isopropanol) | H | 2-methyl-4-(CH₂NH₂)-C₆H₃- | CH₃ | CH₃ | H |
| 27. | (CH₃)₂CH-OH | H | -CH₂CH₂CH₂NH₂ | -CH₂-CH₂- | | H |

EXAMPLE 21

Preparation of Pharmaceutical Compositions

One such unit dosage form is prepared by mixing 120 mg of 1,1-dimethyl-1-carba-2-(cyclopropyl)-6-(1′-hydroxyethyl)-pen-2-em-3-carboxylic acid with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 1,1-dimethyl-1-carba-2-(cyclopropyl)-6-(1′-hydroxyethyl)-pen-2-em-3-carboxylic acid | 125 mg. |
| Cornstarch, U.S.P. | 6 mg. |
| Dicalcium Phosphate | 192 mg. |
| Lactose, U.S.P. | 190 mg. |
| Magnesium Stearate | Balance |

The active ingredient is blended with the dicalcium phosphate, lactose and about half of the cornstarch. The mixture is then granulated with 15% cornstarch paste (6 mg.) and rough-screened. It is dried at 45° C. and screened again through NO. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 1,1-dimethyl-1-carba-2-cyclopropyl)-6-(1′-hydroxyethyl)-pen-2-em-3-carboxylic acid | 500 mg. |
| Sterile water | 2 ml. |
| OPTHALMIC SOLUTION | |
| 1,1-dimethyl-1-carba-2-cyclopropyl)-6-(1′-hydroxyethyl)-pen-2-em-3-carboxylic acid | 100 mg. |
| Hydroxypropylmethyl cellulose | 5 mg. |
| Sterile water to | 1 ml. |
| OTIC SOLUTION | |
| 1,1-dimethyl-1-carba-2-cyclopropyl)-6-(1′-hydroxyethyl)-pen-2-em-3-carboxylic acid | 100 mg. |
| Benzalkonium chloride | 0.1 mg. |
| Sterile water to | 1 ml. |
| TOPICAL OINTMENT | |
| 1,1-dimethyl-1-carba-2-cyclopropyl)-6-(1′-hydroxyethyl)-pen-2-em-3-carboxylic acid | 100 mg. |
| Polyethylene glycol 4000 U.S.P. | 400 mg. |
| Polyethylene glycol 400 U.S.P | 1.0 gram. |

What is claimed is:

1. A compound having the structure:

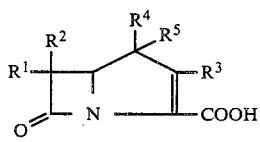

and the pharmaceutically acceptable salts and esters thereof; wherein $R^1$, $R^2$, $R^3$, $R^4$ and $R^5$ are independently selected from the group consisting of hydrogen, and substituted and unsubstituted: alkyl having 1–6 carbon atoms, aralkyl, alkenyl and alkynyl having 2–6 carbon atoms, aryl and aralkyl having 6–10 ring carbon atoms and 1–6 carbon atoms in the alkyl chain, heterocyclyl, heterocyclylthio ($R^3$ is excluded) and heterocyclylalkyl having 1–5 hetero atoms selected from O, N or S in the ring and 1–6 carbon atoms in the alkyl chain, cycloalkyl, spirocycloalkyl, and cycloalkylalkyl having 3 to 6 ring carbon atoms and 1–6 carbon atoms in the alkyl moiety; wherein the substituents on $R^1$, $R^2$, $R^3$, $R^4$ and $R^5$ are selected from chloro, bromo, fluoro, iodo, hydroxyl, amino, mono-, di- and tri-alkyl substituted amino (each alkyl having 1–6 carbon atoms) alkoxyl having 1–6 carbon atoms, guanidino, cyano, amidino and carboxyl; with the proviso that $R^4$, $R^5$ and $R^3$ are not hydrogen.

2. A compound according to claim 1 wherein $R^5$ and $R^4$ are alkyl, having 1–6 carbon atoms, spirocyclopropyl, benzyl or phenyl; $R^1$ is hydrogen and $R^2$ is substituted or unsubstituted: alkyl having 1–6 carbon atoms or phenylalkyl; wherein the substituent is OH or $NH_2$; and $R^3$ is selected from:

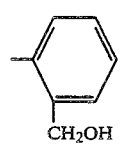 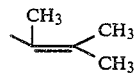

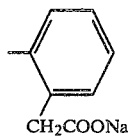 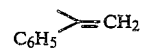

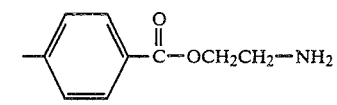 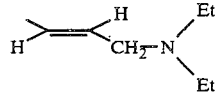

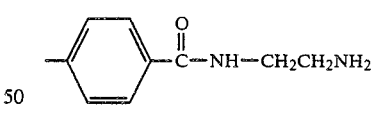 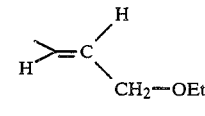

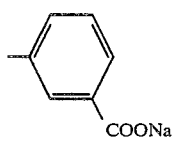 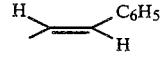

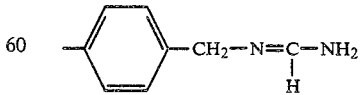 

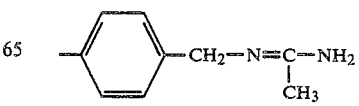 

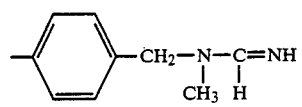 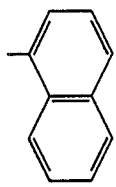

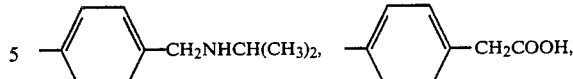 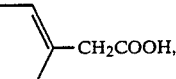

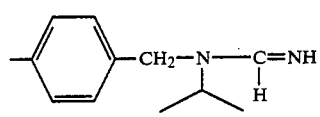 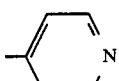

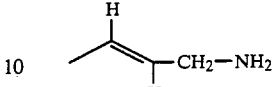 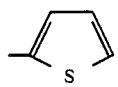

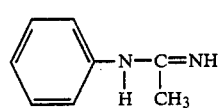 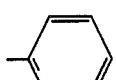

 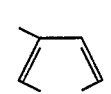

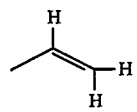 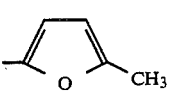

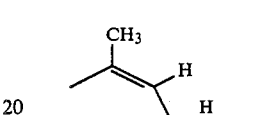 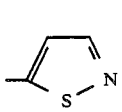

3. A compound according to claim 2 wherein $R^4$ and $R^5$ are methyl, ethyl, isopropyl, cyclopropyl, t-butyl or phenyl; $R^2$ is 1-hydroxyethyl, methyl, or hydroxymethyl; and $R^1$ is hydrogen.

4. A compound according to claims 1, 2 or 3 wherein $R^3$ is selected from the group consisting of:

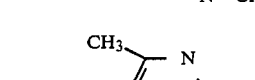 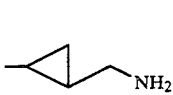

—CH₂CH₂CH₂NH₂,   —CH₂CH₂NH₂, —CH₃,

—CH₂CH₂CH₂OH,    —CH₂CH₂COOH,

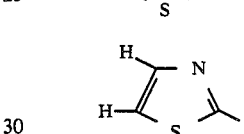

—CH₂CH=CH—SCH₃,

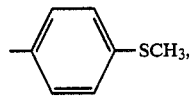

—CH=CHCH₂CH₂NH₂,

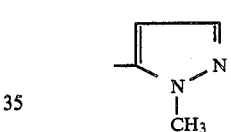 

—CH₂CH₂CH₂CH₂NH₂,

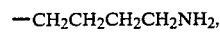 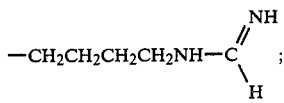

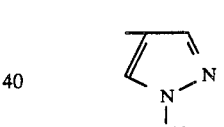 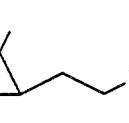

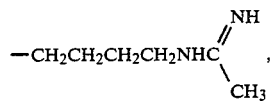 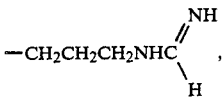

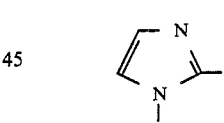 

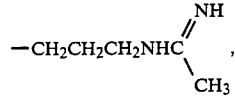 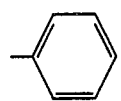

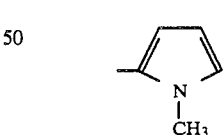 

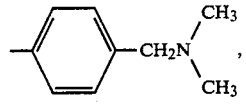 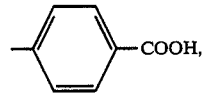

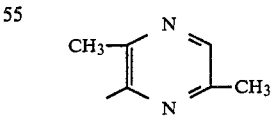 

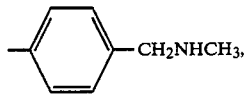 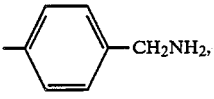

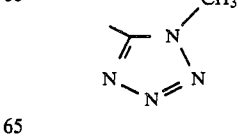 

5. A compound according to claim 4 wherein $R^4$ and $R^5$ are alkyl having 1-6 carbon atoms, phenyl, cyclopropyl, or spirocyclopropyl.

6. A compound according to claim 1 selected from:
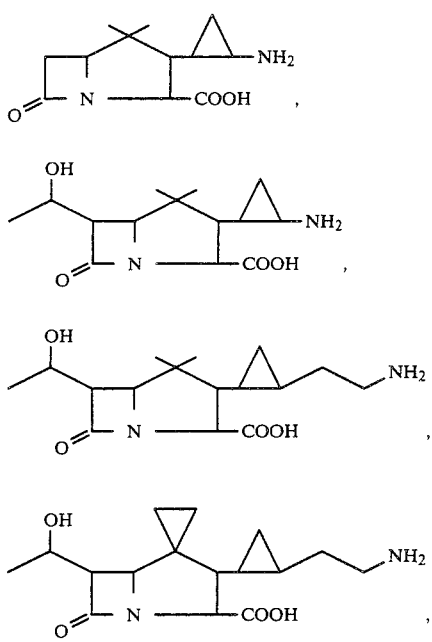
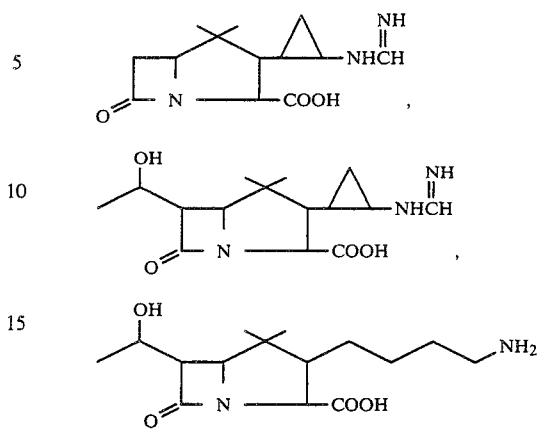
7. An antibiotic pharmaceutical composition comprising a therapeutically effective amount of a compound according to claims 1, 2, 3, 4, 5, or 6 and a pharmaceutical carrier therefor.
8. A method of treatment comprising administering an antibiotically effective amount of a compound according to claims 1, 2, 3, 4, 5, or 6.
* * * * *